(12) United States Patent
Ganz et al.

(10) Patent No.: US 6,551,310 B1
(45) Date of Patent: Apr. 22, 2003

(54) SYSTEM AND METHOD OF TREATING ABNORMAL TISSUE IN THE HUMAN ESOPHAGUS

(76) Inventors: Robert A. Ganz, 1431 Lakeview Ave., Minneapolis, MN (US) 55416; Brian D. Zelickson, 2764 Drew Ave. S., Minneapolis, MN (US) 55416; Roger A. Stern, 10418 Palo Vista Rd., Cupertino, CA (US) 95014

( * ) Notice: Subject to any disclaimer, the term of this patent is extended or adjusted under 35 U.S.C. 154(b) by 0 days.

(21) Appl. No.: 09/714,344

(22) Filed: Nov. 16, 2000

Related U.S. Application Data

(60) Provisional application No. 60/165,687, filed on Nov. 16, 1999.

(51) Int. Cl.[7] ............................................... A61B 18/18
(52) U.S. Cl. .......................................... 606/41; 606/34
(58) Field of Search ............................... 606/41, 7, 10, 606/27–34

(56) References Cited

U.S. PATENT DOCUMENTS

| | | | |
|---|---|---|---|
| 4,658,836 A | 4/1987 | Turner | 128/804 |
| 4,674,481 A | 6/1987 | Boddie et al. | 128/1.3 |
| 4,776,349 A | 10/1988 | Nashef et al. | 128/786 |
| 4,949,147 A | 8/1990 | Bacuvier | 357/38 |
| 4,955,377 A * | 9/1990 | Lennox et al. | 606/27 |
| 4,979,948 A | 12/1990 | Geddes et al. | 606/33 |
| 5,006,119 A | 4/1991 | Acker et al. | 606/27 |
| 5,045,056 A | 9/1991 | Behl | 604/49 |
| 5,117,828 A | 6/1992 | Metzger et al. | 128/642 |
| 5,151,100 A * | 9/1992 | Abele et al. | 606/28 |
| 5,428,658 A | 6/1995 | Oettinger et al. | 378/119 |
| 5,456,682 A | 10/1995 | Edwards et al. | 606/31 |
| 5,496,271 A | 3/1996 | Burton et al. | 604/54 |
| 5,505,730 A | 4/1996 | Edwards | 606/41 |
| 5,514,130 A | 5/1996 | Baker | 606/41 |
| 5,542,916 A | 8/1996 | Hirsch et al. | 604/22 |
| 5,566,221 A | 10/1996 | Smith et al. | 378/145 |
| 5,599,345 A | 2/1997 | Edwards et al. | 606/41 |
| 5,621,780 A | 4/1997 | Smith et al. | 378/65 |
| 5,658,278 A | 8/1997 | Imran et al. | 606/41 |
| 5,713,942 A | 2/1998 | Stern et al. | 607/98 |
| 5,748,699 A | 5/1998 | Smith | 378/65 |
| 5,861,036 A | 1/1999 | Godin | 623/12 |
| 5,891,134 A * | 4/1999 | Goble et al. | 606/27 |
| 5,895,355 A * | 4/1999 | Schaer | 600/381 |
| 5,964,755 A | 10/1999 | Edwards | 606/41 |
| 6,006,755 A | 12/1999 | Edwards | 128/898 |
| 6,033,397 A * | 3/2000 | Laufer et al. | 604/105 |
| 6,041,260 A * | 3/2000 | Stern et al. | 607/98 |
| 6,053,913 A * | 4/2000 | Tu et al. | 600/585 |
| 6,071,277 A * | 6/2000 | Farley et al. | 604/113 |
| 6,073,052 A | 6/2000 | Zelickson et al. | |
| 6,086,558 A | 7/2000 | Bower et al. | 604/96 |
| 6,092,528 A | 7/2000 | Edwards | |
| 6,095,966 A | 8/2000 | Chornenky et al. | 600/3 |
| 6,102,908 A * | 8/2000 | Tu et al. | 606/194 |
| 6,112,123 A | 8/2000 | Kelleher et al. | |

(List continued on next page.)

FOREIGN PATENT DOCUMENTS

| | | |
|---|---|---|
| WO | WO 99/42046 | 8/1999 |
| WO | WO 99/55245 | 11/1999 |
| WO | WO 00/59393 | 10/2000 |

*Primary Examiner*—Roy D. Gibson
*Assistant Examiner*—P Vrettakos
(74) *Attorney, Agent, or Firm*—Paul Davis; Heller Ehrman White & McAuliffe

(57) ABSTRACT

An ablation catheter system and method of use is provided to endoscopically access portions of the human esophagus experiencing undesired growth of columnar epithelium. The ablation catheter system and method includes controlled depth of ablation features and use of either radio frequency spectrum, non-ionizing ultraviolet radiation, warm fluid or microwave radiation, which may also be accompanied by improved sensitizer agents.

28 Claims, 4 Drawing Sheets

U.S. PATENT DOCUMENTS

| | | | |
|---|---|---|---|
| 6,123,703 A * | 9/2000 | Tu et al. ........................ 606/41 |
| 6,123,718 A * | 9/2000 | Tu et al. ........................ 606/41 |
| 6,138,046 A | 10/2000 | Dalton ....................... 600/476 |
| 6,254,598 B1 | 7/2001 | Edwards et al. |
| 6,273,886 B1 | 8/2001 | Edwards et al. |
| 6,321,121 B1 * | 11/2001 | Zelickson et al. .......... 607/101 |
| 6,355,031 B1 | 3/2002 | Edwards et al. |
| 6,355,032 B1 | 3/2002 | Hovda et al. |
| 6,363,937 B1 | 4/2002 | Hovda et al. |
| 6,402,744 B2 | 6/2002 | Edwards et al. |
| 6,405,732 B1 * | 6/2002 | Edwards ..................... 128/898 |
| 6,423,058 B1 | 7/2002 | Edwards et al. |
| 6,440,128 B1 | 8/2002 | Edwards et al. |
| 6,464,697 B1 | 10/2002 | Edwards et al. |

* cited by examiner weight: 400;"># SYSTEM AND METHOD OF TREATING ABNORMAL TISSUE IN THE HUMAN ESOPHAGUS

CROSS-REFERENCE TO RELATED APPLICATIONS

This application claims the benefit of U.S. Provisional Application No. 60/165,687, filed Nov. 16, 1999.

FIELD OF THE INVENTION

A system and method for treating abnormal epithelium in an esophagus.

BACKGROUND OF THE INVENTION

Two of the major functions of the human esophagus are the transport of food from intake to the stomach and the prevention of retrograde flow of gastrointestinal contents. The retrograde flow is, in part, prevented by two esophageal sphincters which normally remain closed and which are functional rather than distinct entities. In particular, a lower esophageal sphincter normally remains closed until parasympathetic activation causes its relaxation, allowing food to pass into the stomach from the esophagus. Various types of food and other activity may cause relaxation of the sphincter, such as fatty meals, smoking and beverages having xanthine content. Certain drugs or pharmaceuticals also may cause relaxation of this lower esophageal sphincter, as well as localized trauma or other problems such as neuromuscular disorders.

Regardless, patients having such difficulties may present with clinical indications including dysphagia, or difficulty in swallowing, as well as more classic symptoms of heartburn and other similar complaints. Recurrent problems of this nature often lead to a disorder known as reflux esophagitis, consisting of esophageal mucosa damage due to the interaction of the gastric or intestinal contents with portions of the esophagus having tissue not designed to experience such interaction. As suggested above, the causative agent for such problems may vary.

The treatment for the underlying cause of such inflammatory mechanisms is not the subject of this patent application, but rather the invention is focused on treatment of secondary damage to tissue in the effected region of the esophagus.

SUMMARY OF THE INVENTION

An ablation catheter and method of use is provided to endoscopically access portions of the human esophagus experiencing undesired growth of columnar epithelium. The ablation catheter system and method includes controlled depth of ablation features and use of either radio frequency spectrum, non-ionizing ultraviolet radiation, warm fluid or microwave radiation, which may also be accompanied by improved sensitizer agents.

DETAILED DESCRIPTION OF THE INVENTION

Figure 1:
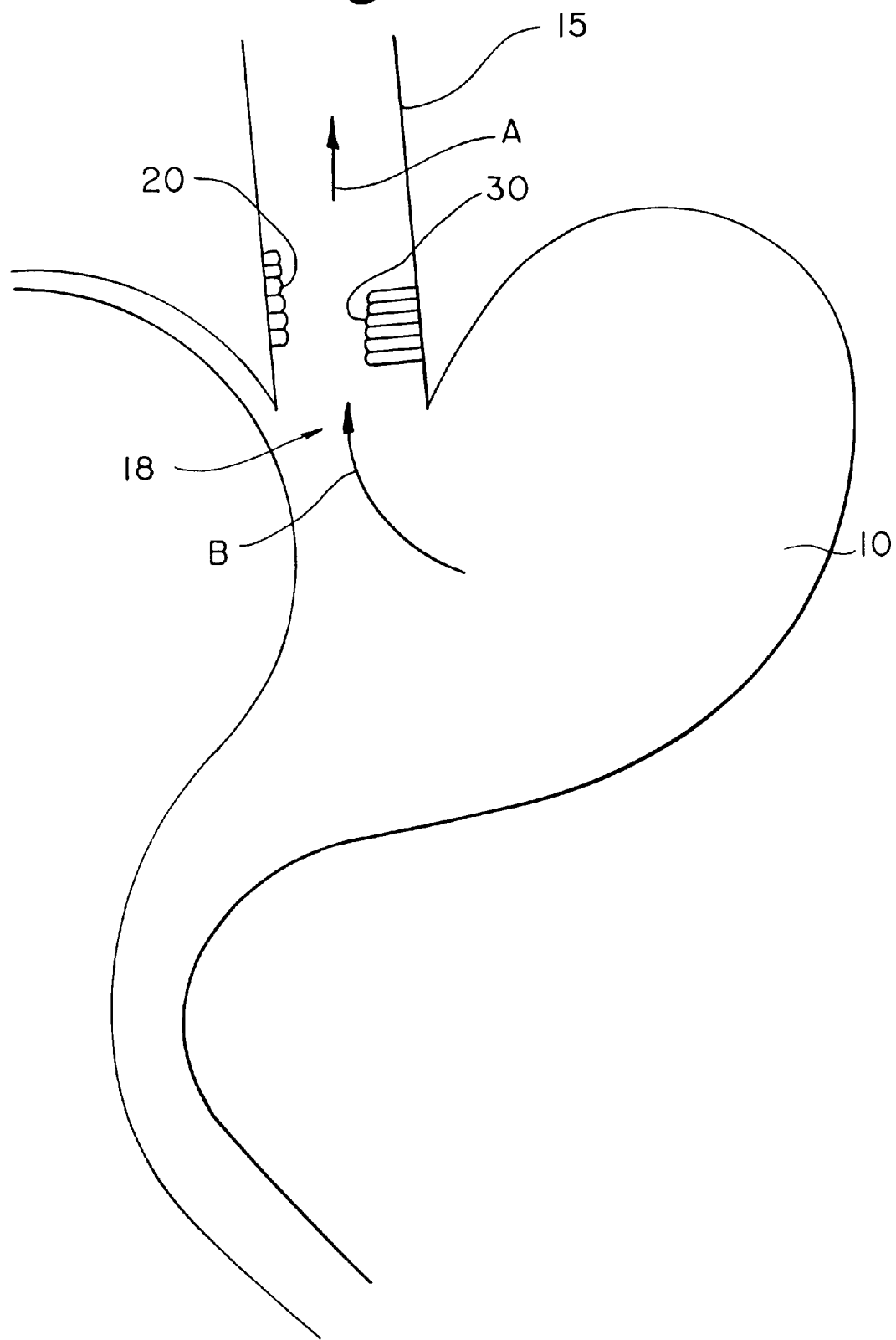
FIG. 1 is a schematic view of portions of an upper digestive tract in a human.

Various inflammatory disorders result in human patients who experience retrograde flow of gastric or intestinal contents from the stomach 10, as shown in FIG. 1, into the esophagus 15. This flow is shown by arrows A and B in FIG. 1. Although the causation of these problems are varied, this retrograde flow may result in secondary disorders which require treatment independent of and quite different from treatments appropriate for the primary disorder—such as disorders of the lower esophageal sphincter 18. One type of inflammatory disorder is known as Barrett's esophagus, in which the stomach acids, bile acids and enzymes regurgitated from the stomach and duodenum enter into the lower esophagus causing damage to the esophageal mucosa. Indeed, when this type of retrograde flow occurs frequently enough, damage may occur to esophageal epithelial cells 20. When normal replacement of damaged cells is overcome by the rate of damage, then the result may be symptomatic destruction of the healthy squamous epithelium. When this occurs, the squamous cells can be replaced by columnar epithelium 30 of the lower esophageal passageway. It is well established that although some of the columnar cells may be benign, others may result in adenocarcinoma. Accordingly, attention has been focused on identifying and removing this columnar epithelium in order to mitigate more severe implications for the patient. Examples of efforts to properly identify these growths, referred to as Barrett's epithelium or more generally as Barrett's esophagus, have included conventional visualization techniques known to practitioners in the field. Although certain techniques have been developed to characterize and distinguish such epithelium cells, such as disclosed in U.S. Pat. Nos. 5,524,622 and 5,888,743, there has yet to be shown efficacious means of accurately removing undesired growths of this nature from portions of the esophagus to mitigate risk of malignant transformation.

Figure 2:
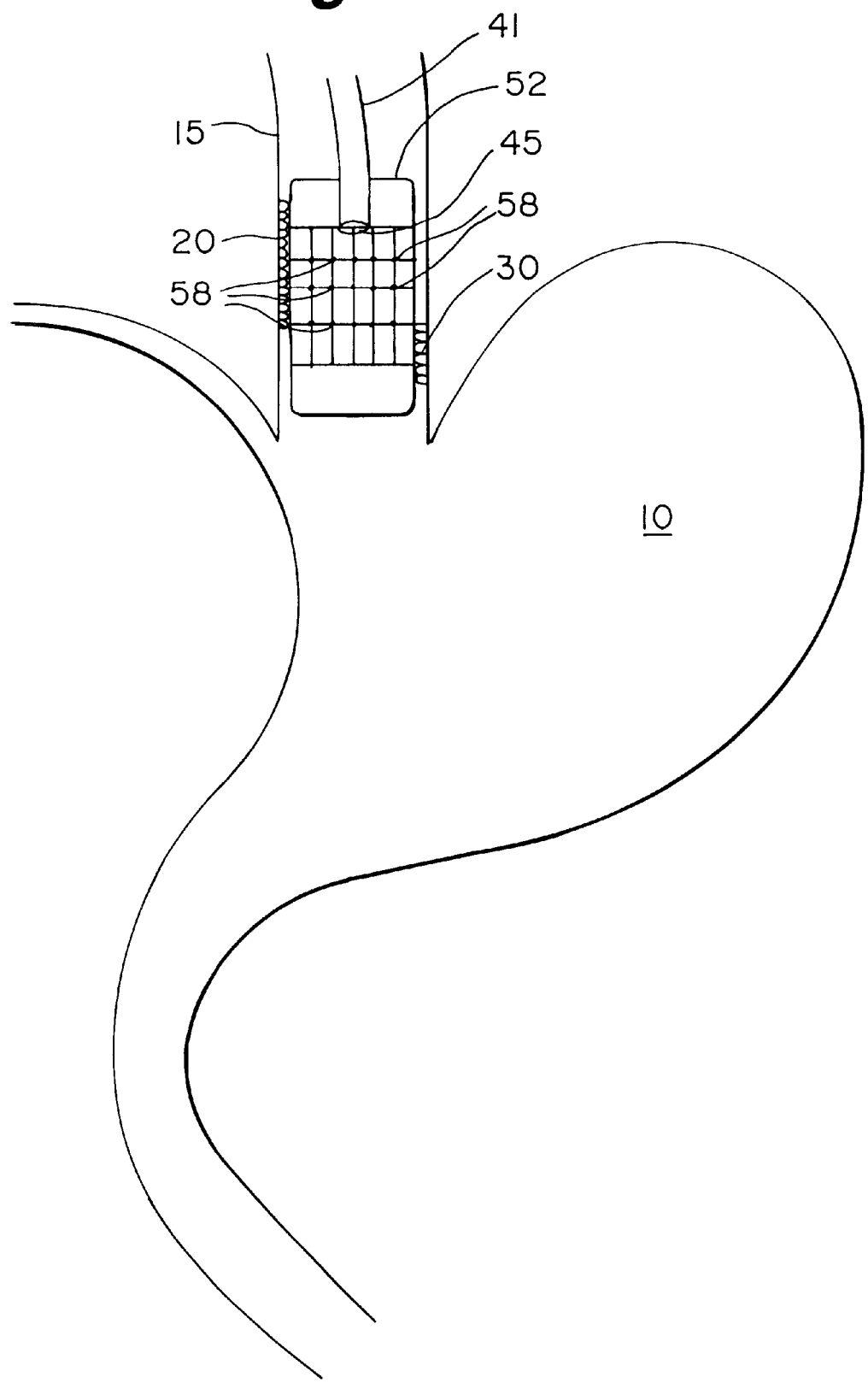
FIG. 2 is a schematic view of a device of the invention, in an expanded mode, within an esophagus.

Means for accomplishing this procedure according to this invention includes use of the radio frequency spectrum at conventional levels to accomplish ablation of mucosal or submucosal level tissue. Such ablation is designed to remove the columnar growths 30 from the portions of the esophagus 15 so effected. In one embodiment, as shown in FIG. 2, an elongated flexible shaft 41 is provided for insertion into the body in any of various ways selected by the medical provider. The shaft may be preferably placed endoscopically, e.g. through the esophagus, or it may be placed surgically, or by other means. Radiant energy distribution means is provided at a distal end 45 of the flexible shaft to provide appropriate energy for ablation as desired. It is recognized that radiant energy of a preferred type includes radio frequency energy, microwave energy, or ultraviolet light, the latter possibly in combination with improved sensitizing agents. It is also recognized that another embodiment of this invention may utilize heatable fluid as an ablation energy medium.

In one embodiment the flexible shaft comprises a coaxial cable surrounded by an electrical insulation layer and comprises a radiant energy distribution means located at its distal end. In one form of the invention, a positioning and distending device around the distal end of the instrument is of sufficient size to contact and expand the walls of the body cavity in which it is placed (e.g. the esophagus) both in the front of the distribution means as well as on the sides of the distribution means. For example, the distal head of the instrument can be supported at a controlled distance from the wall of the esophagus by an expandable balloon member 52 so as to regulate and control the amount of energy transferred to the tissue comprising the esophageal wall. The balloon is preferably bonded to a portion of the flexible shaft at a point spaced from the distal head means.

Another embodiment comprises using the distending or expandable balloon member as the vehicle to deliver the ablation energy. A critical feature of this embodiment includes means by which the energy is transferred from the distal head portion of the invention to the membrane comprising the balloon member. For example, one type of energy distribution that may be appropriate and is incorporated herein in its entirety is shown in U.S. Pat. No. 5,713,942, in which an expandable balloon is connected to a power source which provides radio frequency power having the desired characteristics to selectively heat the target tissue to a desired temperature. The balloon 52 of the current invention may be constructed of an electroconductive elastomer such as a mixture of polymer, elastomer, and electroconductive particles, or it may comprise a nonextensable bladder having a shape and a size in its fully expanded form which will extend in an appropriate way to the tissue to be contacted. In another embodiment, an electroconductive member may be formed from an electroconductive elastomer wherein an electroconductive material such as copper is deposited onto a surface and an electrode pattern is etched into the material and then the electroconductive member is attached to the outer surface of the balloon member. In one embodiment, the electroconductive member, e.g. the balloon member 52, has a configuration expandable in the shape to conform to the dimensions of the expanded (not collapsed) inner lumen of the human lower esophageal tract. In addition, such electroconductive member may consist of a plurality of electrode area segments 58 having thermistor means or the like associated with each electrode segment by which the temperature from each of a plurality of segments is monitored and controlled by feedback arrangement. In another embodiment, it is possible that the electroconductive member may have means for permitting transmission of microwave energy to the ablation site. In yet another embodiment, the distending or expandable balloon member may have means for carrying or transmitting a heatable fluid within one or more portions of the member so that the thermal energy of the heatable fluid may be used as the ablation energy source.

A preferred device, such as that shown in FIG. 2, includes steerable and directional control means, a probe sensor for accurately sensing depth of cautery, and appropriate alternate embodiments so that in the event of a desire not to place the electroconductive elements within the membrane forming the expandable balloon member it is still possible to utilize the balloon member for placement and location control while maintaining the energy discharge means at a location within the volume of the expanded balloon member, such as at a distal energy distribution head of conventional design.

In one embodiment, the system disclosed herein may be utilized as a procedural method of treating Barrett's esophagus. This method includes the detection and diagnosis of undesired columnar epithelium within the esophagus. After determining that the portion or portions of the esophagus having this undesired tissue should be partially ablated, then the patient is prepared as appropriate according to the embodiment of the device to be utilized. Then, the practitioner prepares the patient as appropriate and inserts, in one embodiment, via endoscopic access and control, the ablation device shown and discussed herein through the mouth of the patient. Further positioning of portions of the device occur until proper location and visualization identifies the ablation site in the esophagus. Selection and activation of the appropriate quadrant(s) or portion(s)/segment(s) on the ablation catheter member is performed by the physician, including appropriate power settings according to the depth of cautery desired. Additional settings may be necessary as further ablation is required at different locations and/or at different depths within the patient's esophagus. Following the ablation, appropriate follow-up procedures as are known in the field are accomplished with the patient during and after removal of the device from the esophagus. The ablation treatment with ultraviolet light may also be accompanied by improved sensitizer agents, such as hematoporphyrin derivatives such as Photofrine® porfimer sodium, registered trademark of Johnson & Johnson Corporation, New Brunswick, N.J.).

In yet another embodiment of the method of the invention, the system disclosed herein may be utilized as a procedural method of treating dysplasia or cancerous tissue in the esophagus. After determining that the portion or portions of the esophagus having undesired tissue which should be partially ablated, then the patient is prepared as appropriate according to the embodiment of the device to be utilized and treatment is provided as described above.

In yet another method of the invention, the practitioner may first determine the length of the portion of the esophagus requiring ablation and then may choose an ablation catheter from a plurality of ablation catheters of the invention, each catheter having a different length of the electrode member associated with the balloon member. For example, if the practitioner determined that 1 centimeter of the esophageal surface required ablation, an ablation catheter having 1 centimeter of the electrode member could be chosen for use in the ablation. The length of the electrode member associated with the balloon member can vary in length from 1 to 10 cm.

In yet another embodiment, a plurality of ablation catheters wherein the radiant energy distribution means are associated with the balloon member can be provided wherein the diameter of the balloon member when expanded varies from 12 mm to 25 mm. In this method, the practitioner will choose an ablation catheter having a diameter when expanded which will cause the esophagus to stretch and the mucosal layer to thin out, thus, reducing blood flow at the site of the ablation. The esophagus normally is 5 to 6 mm thick, with the method of the invention the esophagus is stretched and thinned so that the blood flow through the esophageal vasculature is occluded. It is believed that by reducing the blood flow in the area of ablation, the heat generated by the radiant energy is less easily dispersed to other areas of the esophagus thus focusing the energy to the ablation site.

One means a practitioner may use to determine the appropriate diameter ablation catheter to use with a particular patient would be to use in a first step a highly compliant balloon connected to pressure sensing means. The balloon would be inserted into the esophagus and positioned at the desired site of the ablation and inflated until an appropriate pressure reading was obtained. The diameter of the inflated balloon would be determined and an ablation device of the invention having a balloon member capable of expanding to that diameter would be chosen for use in the treatment. It is well known that the esophagus may be expanded to a pressure of 60–120 lbs./square inch. In the method of this invention, it is desirable to expand the expandable electroconductive member such as a balloon sufficiently to occlude the vasculature of the submucosa, including the arterial, capillary or venular vessels. The pressure to be exerted to do so should therefore be greater than the pressure exerted by such vessels.

Figure 3:
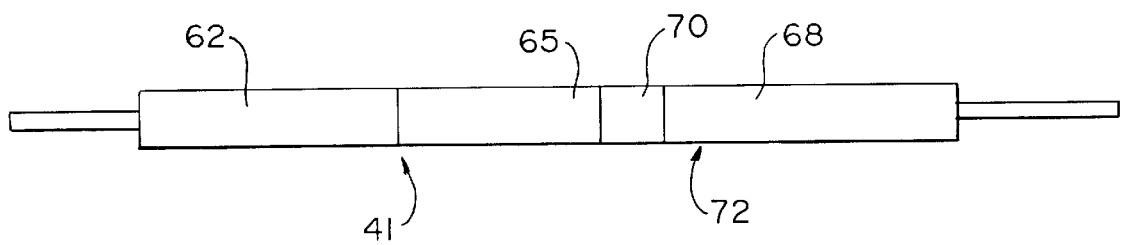
FIG. 3 is a schematic view of a device of the invention.
Figure 4:
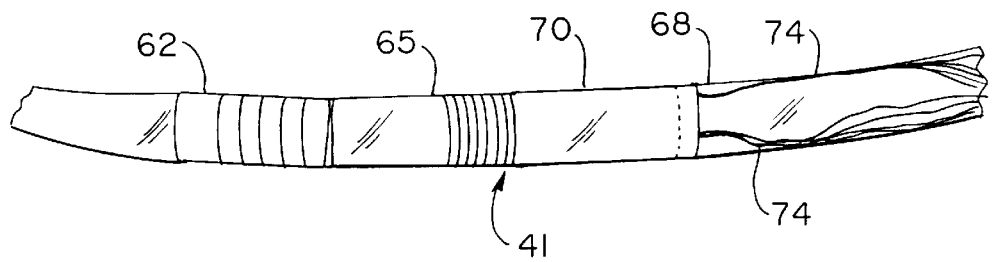
FIG. 4 is a photograph of the device of FIG. 3.
Figure 5:
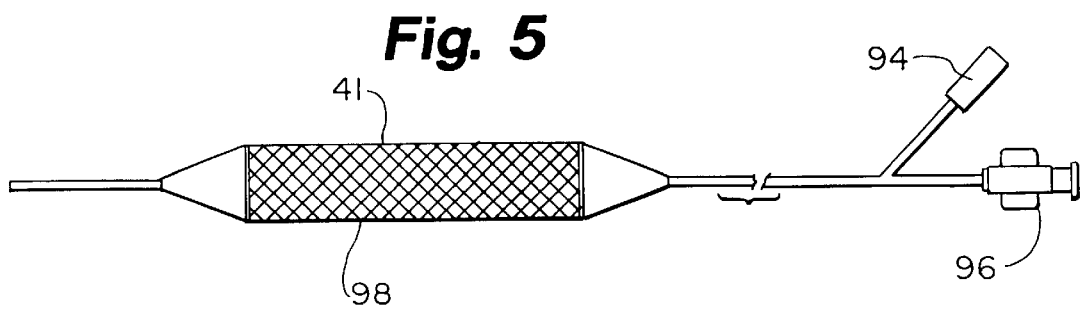
FIG. 5 is a view of a device of the invention.
Figure 6A:
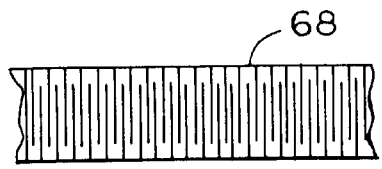
FIG. 6 shows the electrode patterns of the device of FIG. 3.
Figure 6B:
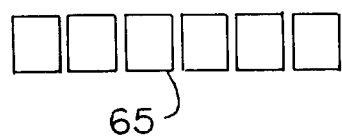
Figure 6C:
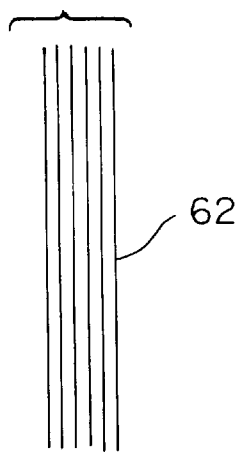
Figure 7A:
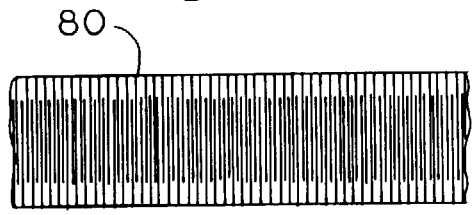
FIG. 7 shows electrode patterns of that may be used with a device of the invention.
Figure 7B:
Figure 7D:
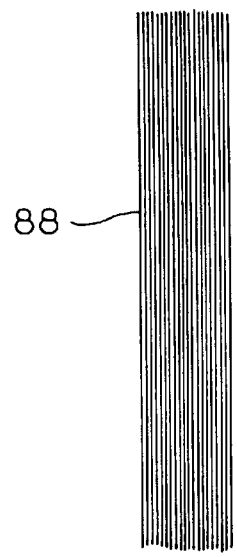
Figure 7C:

Operation and use of a device of the invention are described as follows. The device used is shown schematically in FIGS. 3 and 5 and a photograph of the device is shown in FIG. 4. As shown in FIG. 5, the elongated flexible shaft 41 is connected to a multi-pin electrical connector 94 which is connected to the power source and includes a male luer connector 96 for attachment to a fluid source useful in expanding the expandable member. The elongated flexible shaft has an electrode 98 wrapped around the circumference. The expandable member of the device shown in FIGS. 3 and 4 further includes three different electrode patterns, the patterns of which are represented in greater detail in FIG. 6. Normally, only one electrode pattern would be used in a device of this invention. In this device, the elongated flexible shaft 41 comprises six bipolar rings 62 with 2 mm separation at one end of the shaft (one electrode pattern), adjacent to the bipolar rings is a section of six monopolar bands or rectangles 65 with 1 mm separation (a second electrode pattern), and another pattern of bipolar axial interlaced finger electrodes 68 is positioned at the other end of the shaft (a third electrode pattern). In this device, a null space 70 was positioned between the last of the monopolar bands and the bipolar axial electrodes. The catheter used in the study was prepared using a polyimide flat sheet of about 1 mil (0.001") thickness coated with copper. The desired electrode patterns were then etched into the copper.

The electrode patterns of the invention may vary, other possible electrode patterns are shown in FIG. 7 as 80, 84, 88, and 92, respectively. Pattern 80 is a pattern of bipolar axial interlaced finger electrodes with 0.3 mm separation. Pattern 84 includes monopolar bands with 0.3 mm separation. Pattern 88 includes bipolar rings with 0.3 mm separation. Pattern 92 is electrodes in a pattern of undulating electrodes with 0.2548 mm separation.

In this case the electrodes were attached to the outside surface of an esophageal dilation balloon 72 having a diameter of 18 mm. The device was adapted to use radio frequency by attaching wires 74 as shown in FIG. 4 to the electrodes to connect them to the power source.

The balloon was deflated and the catheter inserted into the esophagus as described below. In addition to the series of three different electrode patterns a number of different energy factors were applied to the esophagus of a normal immature swine (about 25 kgs). First, an endoscope was passed into the stomach of the subject. The device of the invention was placed into the distal esophagus using endoscopic guidance. The balloon member was inflated to press the electrodes against the esophageal mucosa. There was no indication that balloon dilation resulted in untoward effects on the esophagus.

Once the balloon member and electrodes were in place the first set of radio frequency ("RF") applications were made. Following endoscopic evaluation of the treated areas, the device was withdrawn proximally. The placement of the device was evaluated endoscopically to assure a gap of normal tissue between the area of the first application and the second application, which gap will assure identification of the two treatment areas during post procedure evaluations. The procedure was repeated a third time using a similar procedure to that of the second application. During the treatment the tissue impedance was monitored as an indicator of the progress of the treatment, high impedance being an indication of desiccation. Accordingly, the practitioner can determine through monitoring the tissue impedance when sufficient ablation has occurred.

The treatment parameters and observations from the first set of RF applications are shown in Table 1. The effect of the treatment was evaluated endoscopically. The areas of the esophagus treated (the "treatment patterns") were clearly visible as white bands. Untreated areas had the normal red/pink color.

TABLE 1

Treatment Set 1: Parameters and Observations

| Device Location & Configuration | Treatment Protocol | Observed Impedance Initial (Ohms)[1] | Terminal (Ohms) |
|---|---|---|---|
| Distal//Bipolar | 25 watts @ 30 secs + 40 watts @ 30 secs | 33 | 258 |
| Monopolar Band 1 | 25 watts @ 30 secs | 125 | Shut off at 29 secs[2] |
| Band 2 | 25 watts @ 30 secs | 107 | Shut off at 20 secs |
| Band 3 | 25 watts @ 30 secs | 125 | Shut off at 25 secs |
| Band 4 | 25 watts @ 30 secs | 105 | Shut off at 22 secs |
| Band 5 | 25 watts @ 30 secs | 125 | Full[3] at 30 secs |
| Band 6 | 25 watts @ 30 secs | 90 | Shut off at 19 secs |
| Proximal//Bipolar | 15 watts @ 30 secs + 40 watts @ 30 secs | No data | No change from baseline |

Transformer tap = 50
Shut off usually occurs at 300 ohms.
"Full" indicates treatment progressed for the entire scheduled interval without an automatic termination event.

As can be seen from the table, once the observed impedance at the ablation site reached 300 ohms the radio frequency generator shut off the signal. The treatment parameters and observations from the second set of RF applications made mid level in the esophagus are shown in Table 2. As before the effect of the treatment was evaluated endoscopically. The treatment patterns were clearly visible.

TABLE 2

Treatment Set 2: Parameters and Observations

| Device Location & Configuration | Treatment Protocol | Observed Impedance Initial (Ohms)[4] | Terminal (Ohms) |
|---|---|---|---|
| Distal//Bipolar | 25 watts @ 60 secs | 30 | 121 (jump at 30 secs) |
| Monopolar Band 1 | 20 watts @ 60 secs | 112 | 103 Full at 60 secs[5] |
| Band 2 | 20 watts @ 60 secs | 108 | 300 Shut off at 25 secs |
| Band 3 | 20 watts @ 60 secs | 109 | 301 Shut off at 31 secs |
| Band 4 | 20 watts @ 60 secs | 108 | 300 Shut off at 27 secs |
| Band 5 | 20 watts @ 60 secs | 115 | 301 Shut off at 42 secs |
| Band 6 | 20 watts @ 60 secs | 109 | 301 Shut off at 24 secs |
| Proximal//Bipolar | 40 watts @ 60 secs | 32 | 37 |

Transformer tap = 50
"Full" indicates treatment progressed for the entire scheduled interval without an automatic termination event.

The treatment parameters and observations from the third set of RF applications are depicted in Table 3. The effect of the treatment was evaluated endoscopically. The treatment patterns were clearly visible as white bands as compared to the normal red/pink color.

TABLE 3

Treatment Set 3: Parameters and Observations

| Device Location & Configuration | Treatment Protocol | Observed Impedance Initial (Ohms)[6] | Terminal (Ohms) |
|---|---|---|---|
| Distal//Bipolar | 25 watts @ 120 secs | 67 | 168 Dec at 106 secs |
| [7]Monopolar Band 1 | 15 watts @ 90 secs | 104 | 283 Full at 90 secs[8] |
| Band 2 | 15 watts @ 90 secs | 110 | 301 Shut off at 37 secs |
| Band 3 | 15 watts @ 90 secs | 115 | 300 Shut off at 43 secs |
| Band 4 | 15 watts @ 90 secs | 105 | 287 Full at 90 secs |
| Band 5 | 15 watts @ 90 secs | 104 | 281 Full at 90 secs |
| Band 6 | 15 watts @ 90 secs | 105 | 289 (inc at 38 secs) |
| Proximal// Bipolar | 40 watts @ 120 secs | 87 | 105 |

Bipolar transformer tap = 35;
Monopolar = 50
Monopolar treatment usually resulted in a dramatic decreased in "watts" read out within the middle and the end of the treatment interval. The decrease was from 15 watts (initial setting) to 3 or 4 watts at the end of the treatment cycle.
"Full" indicates treatment progressed for the entire scheduled interval without an automatic termination event.

The treatment transformer tap was changed for the bipolar treatments from 50 to 35. Of note is the observation that towards the end of the monopolar treatments, the watts output as reported on the generator decreased from a setting of 15 watts to a reading of 3 to 4 watts. The increase in impedance observed in the study may be useful as an endpoint for controlling the RF energy at the ablation site.

The RF energy can be applied to the electroconductive members in a variety of ways. In one embodiment, it is applied in the bipolar mode to the bipolar rings through simultaneous activation of alternating rings. In another embodiment, it is applied to the bipolar rings through sequential activation of pairs of rings. In another embodiment, the RF energy can be applied in monopolar mode through sequential activation of individual monopolar bands or simultaneous activation of the monopolar bands.

After the treatment of the swine esophagus as described above using radio frequency, the esophagus was extirpated and fixed in 10 percent normal buffered formalin (NBF). Three distinct lesion areas were observed corresponding to the three treatment sites and the esophagus was divided into three sections that approximated the three treatment zones. Each segment was cut into 4 to 5 mm thick serial cross sections. Selected sections from each treatment segment were photographed and the photographs of representative treatment segments were assembled side by side to compare similar catheter electrode patterns among the three treatment regimens. The following observations were made. Almost all the treated segments demonstrated necrosis of the mucosa. Changes with the submucosal, muscularis and adventitial layers were observed, typically demonstrated by tissue discoloration suggestive of hemorrhage within the tissue. Finally in comparing the tissue to the normal esophageal morphology, most treated segments were dilated with thinned walls. Thus, all the electrode patterns and treatment parameters resulted in ablation of the mucosal layer of the esophagus.

The treated esophagus was sectioned into 44 sections with each section labeled as either a treatment region or a region adjacent to a treatment region. Each section was processed for histological examination and stained with H&E and reviewed twice. The following parameters were estimated and noted.

a. Percent Epithelial Slough:
   Slough was defined as a separation of one or more layers of the epithelium as visualized at 100-× magnification.
b. Epith: Percent cell death:
   The basal layers of the epithelium were reviewed at 400-× magnification.
   Determination of "cell death" was based upon the following criteria:
      Condensation of the nuclear material.
      Loss of well-defined nuclear outline.
      Loss of well-defined cellular detail.
c. *Lamina propria*//*Muscularis mucosa*//Submucosa: Percent death:
   Cell death was based primarily on the condensation of nuclear material.
d. Muscularis/Adventitia:
   Same as above.

The following table summarizes the percent slough, percent death in the mucosa and submucosa and percent death in the muscularis as determined during the above-described study.

TABLE 4

| Section Number | Section Location | Percent Slough | Percent death// Mucosa & submucosa | Percent death// Muscularis |
|---|---|---|---|---|
| 1 | Distal spacer | 0 | 0 | 0 |
| 2 | Distal//Bipolar Ring | 0 | 0 | 0 |
| 3 | Distal//Bipolar Ring | 33 | 100 | 75 |
| 4 | Distal//Bipolar Ring | 100 | 100 | 50 |
| 5 | Distal//Monopolar Band | 100 | 100 | 75 |
| 6 | Distal//Monopolar Band | 100 | 100 | 75 |
| 7 | Distal//Null band | 100 | 100 | 50 |
| 8 | Distal//Null band | 100 | 100 | 75 |
| 9 | Distal//Bipolar axial | 50 | 95 | 50 |
| 10 | Distal//Bipolar axial | 75 | 90 | 25 |
| 11 | Distal//Bipolar axial | 50 | 75 | 25 |
| 12 | Distal//Bipolar axial | 50 | 75 | 25 |
| 13 | Distal//Bipolar axial | 50 | 100 | 25 |
| 14 | Distal ◊ Mid spacer | 0 | 0 | 0 |
| 15 | Distal ◊ Mid spacer | 0 | 0 | 0 |
| 16 | Distal ◊ Mid spacer | 0 | 0 | 0 |
| 17 | Distal ◊ Mid spacer | 0 | 0 | 0 |
| 18 | Distal ◊ Mid spacer | 5 | 5 | 5 |
| 19 | Mid tmt//Bipolar ring | 75 | 100 | 25 |
| 20 | Mid tmt//Bipolar ring | 60 | 100 | 25 |
| 21 | Mid tmt//Bipolar ring | 90 | 100 | 25 |
| 22 | Mid tmt//Monopolar band | 60 | 75 | 25 |
| 23 | Mid tmt//Null band | 65 | 95 | 10 |
| 24 | Mid tmt//Null band | 75 | 100 | 10 |
| 25 | Mid tmt//Bipolar axial | 65 | 95 | 10 |
| 26 | Mid tmt//Bipolar axial | 35 | 25 | 25 |
| 27 | Mid tmt//Bipolar axial | 25 | 25 | 10 |
| 28 | Mid tmt//Bipolar axial | 30 | 50 | 25 |
| 29 | Mid tmt ◊ proximal spacer | 65 | 25 | 50 |
| 30 | Proximal//Bipolar ring | 50 | 75 | 50 |
| 31 | Proximal//Bipolar ring | 25 | 75 | 25 |
| 32 | Proximal//Bipolar ring | 50 | 80 | 25 |
| 33 | Proximal//Bipolar ring | 75 | 75 | 50 |

TABLE 4-continued

| Section Number | Section Location | Percent Slough | Percent death// Mucosa & submucosa | Percent death// Muscularis |
|---|---|---|---|---|
| 34 | Proximal//Monopolar band | 90 | 50 | 50 |
| 35 | Proximal//Monopolar band | 100 | 99 | 75 |
| 36 | Proximal//Monopolar band | 100 | 100 | 75 |
| 37 | Proximal//Null band | 90 | 95 | 75 |
| 38 | Proximal//Bipolar axial | 50 | 25 | 50 |
| 39 | Proximal//Bipolar axial | 90 | 50 | 50 |
| 40 | Proximal//Bipolar axial | 100 | 75 | 75 |
| 41 | Proximal//Bipolar axial | 90 | 90 | 50 |
| 42 | Proximal spacer | 0 | 0 | 0 |
| 43 | Proximal spacer | 0 | 0 | 0 |
| 44 | Proximal spacer | 0 | 0 | 0 |

Various modifications to the above-mentioned treatment parameters can be made to optimize the ablation of the abnormal tissue. To obtain shallower lesions than the ones obtained in the in the above-mentioned study the RF energy applied may be increased while decreasing the treatment time. Also, the electrode patterns may be modified such as shown in FIG. 7 to improve the evenness and shallowness of the resulting lesions. The system and method of the invention may also be modified to incorporate temperature feedback, resistance feedback and/or multiplexing electrode channels.

While a preferred embodiment of the present invention has been described, it should be understood that various changes, adaptations and modifications may be made therein without departing from the spirit of the invention and the scope of the appended claims.

What is claimed is:

1. A system for ablation of abnormal tissue from a human esophagus, comprising:
   an elongated member;
   an expandable member coupled to a distal portion of the elongated member and sized to be positioned and expanded in the esophagus; and
   a plurality of RF electrode pairs at least partially extending around a circumference of the expandable member, a width of each RF electrode and a spacing between adjacent RF electrodes selected to provide a selectable ablation of an esophagus mucosal layer, a spacing between adjacent RF electrodes being no more than 2 mm, and the plurality of REF electrode pairs being arranged in a pattern.

2. The system of claim 1, wherein the expandable member is a balloon.

3. The system of claim 1, wherein the plurality of RF electrode pairs form an RF electrode array.

4. The system of claim 1, further comprising:
   an RF power source coupled to the plurality of RF electrode pairs.

5. The system of claim 1, further comprising:
   a control device coupled to the plurality of RF electrode pairs, the control device providing controlled positioning of the expandable member.

6. The system of claim 1, wherein the expandable member is sized in an expanded state to stretch the esophagus and thin a mucosal layer of the esophagus.

7. The system of claim 1, further comprising:
   an expandable medium source coupled to the expandable member.

8. The system of claim 1, wherein the plurality of RF electrode pairs are in a pattern.

9. A system for ablation of abnormal tissue from a human esophagus, comprising:
   an elongated member;
   an expandable member coupled to a distal portion of the elongated member and sized to be positioned and expanded in the esophagus; and
   a plurality of RF electrode pairs at least partially extending around a circumference of the expandable member, the plurality of RF electrodes being arranged in a pattern of bipolar axial interlaced finger electrodes, a width of each RF electrode and a spacing between adjacent RF electrodes selected to provide a selectable ablation of an esophagus mucosal layer.

10. A system for ablation of abnormal tissue from a human esophagus, comprising:
    an elongated member;
    an expandable member coupled to a distal portion of the elongated member and sized to be positioned and expanded in the esophagus; and
    a plurality of RF electrode pairs at least partially extending around a circumference of the expandable member, the plurality of RF electrodes being arranged in a pattern of RF monopolar electrodes, a width of each RF electrode and a spacing between adjacent RF electrodes selected to provide a selectable ablation of an esophagus mucosal layer.

11. The system of claim 1, wherein each of an RF electrode in the plurality of RF electrode pairs is parallel to an adjacent RF electrode.

12. The system of claim 1, wherein the plurality of RF electrode pairs are formed on a sheet coupled to the expandable member.

13. The system of claim 1, further comprising:
    a temperature sensor coupled to the plurality of RF electrode pairs.

14. The system of claim 1, further comprising:
    a multiplexer coupled to the plurality of RF electrode pairs.

15. The system of claim 1, wherein the expandable member is made of a electroconductive elastomer.

16. The system of claim 1, wherein the plurality of RF electrode pairs has a length in the range of 1 to 10 cm.

17. The system of claim 1, wherein in an expanded state, the expandable member has a dimater in the range of 12 to 25 mm.

18. The system of claim 1, further comprising:
    a multiple-pin electrical connector coupled to the plurality of RF electrode pairs.

19. The system of claim 1, wherein the elongated member is flexible.

20. The system of claim 1, wherein the expandable member is expandable to a fixed size in the expandable state.

21. The system of claim 1, wherein the expandable member is expandable to a variable size in the expandable state.

22. The system of claim 1, wherein the expandable member in an expandable state is sized to provide sufficient stretching of an esophagus to impede blood flow in an esophagus vasculature.

23. A system for ablation of abnormal tissue from a human esophagus, comprising:
    an elongated member;
    an expandable member coupled to a distal portion of the elongated member and sized to be positioned and expanded in the esophagus; and a plurality of bipolar RF electrode pairs at least partially extending around a circumference of the expandable member, a width of each RF electrode and a spacing between adjacent RF electrodes in a pair selected to provide a selectable ablation of an esophagus mucosal layer, the plurality of RF electrodes being arranged in a pattern of bipolar axial interlaced finger electrodes, wherein a spacing of electrodes in an electrode pair is 2 mm or less.

24. The system of claim 23, wherein the RF electrodes are configured to provide a power in the range of 50 to 60 Watts per square centimeter.

25. The system of claim 24, wherein the RF electrodes are configured to provide an energy of at least 10 Joules per square centimeter.

26. A system for ablation of abnormal tissue from a human esophagus, comprising:

an elongated member;

an expandable member coupled to a distal portion of the elongated member and sized to be positioned and expanded in the esophagus; and a plurality of RF electrode at least partially extending around a circumference of the expandable member, a width of each RF electrode and a spacing between adjacent RF electrodes selected to provide a selectable ablation of an esophagus mucosal layer, the RF electrodes being arranged as a contiguous sequence of arrays and a spacing between adjacent RF electrodes being no more than 2 mm.

27. The system of claim 26, wherein the arrays have a length of at least 1 m.

28. A system for ablation of abnormal tissue from a human esophagus, comprising:

an elongated member;

an expandable member coupled to a distal portion of the elongated member and sized to be positioned and expanded in the esophagus; and a plurality of bipolar RF electrode pairs at least partially extending around a circumference of the expandable member, a width of each RF electrode and a spacing between adjacent RF electrodes is selected to provide a selectable ablation of an esophagus mucosal layer, a spacing between adjacent RF electrodes being no more than 2 mm, the RF electrodes being arranged as a contiguous sequence of arrays with a single common RF electrode along an entire length of the arrays, each electrode pair having an electrode that is divided into a sequence of selectable lengths.

\* \* \* \* \*

UNITED STATES PATENT AND TRADEMARK OFFICE
CERTIFICATE OF CORRECTION

| | | |
|---|---|---|
| PATENT NO. | : 6,551,310 B1 | Page 1 of 1 |
| APPLICATION NO. | : 09/714344 | |
| DATED | : April 22, 2003 | |
| INVENTOR(S) | : Robert A. Ganz et al. | |

It is certified that error appears in the above-identified patent and that said Letters Patent is hereby corrected as shown below:

In claim 1, at Column 9, line 49, please change:
"REF" to --RF--.

Signed and Sealed this
First Day of February, 2011

David J. Kappos
*Director of the United States Patent and Trademark Office*